United States Patent [19]

Bellet et al.

[11] Patent Number: 4,804,626

[45] Date of Patent: Feb. 14, 1989

[54] IMMUNOMETRIC ASSAY FOR THE DETECTION OF HUMAN CHORIONIC GONADOTROPIN

[75] Inventors: Dominique Bellet, Paris, France; Jack R. Wands, Waban; Mehmet Ozturk, Boston, both of Mass.

[73] Assignee: The General Hospital Corporation, Boston, Mass.

[21] Appl. No.: 921,508

[22] Filed: Oct. 22, 1986

[51] Int. Cl.$^4$ .......................................... G01N 33/577
[52] U.S. Cl. .................................. 435/7; 435/240.27; 435/810; 436/510; 436/531; 436/534; 436/548; 436/800; 436/804; 436/808; 436/813; 436/814; 436/818; 436/819; 530/387; 530/808; 530/809
[58] Field of Search .................... 435/7, 240, 27, 810; 436/510, 531, 534, 548, 800, 804, 808, 813, 814, 818, 819; 530/387, 808, 809

[56] References Cited

U.S. PATENT DOCUMENTS

| | | | |
|---|---|---|---|
| 3,867,517 | 2/1975 | Ling | 424/1.1 |
| 4,098,876 | 4/1978 | Piasio et al. | 424/1 |
| 4,376,110 | 3/1983 | David et al. | 436/513 |
| 4,486,530 | 12/1984 | David et al. | 436/548 |
| 4,565,687 | 1/1986 | Khazaeli et al. | 435/7 |

OTHER PUBLICATIONS

Mizuchi et al, "Monoclonal Antibodies to Human Chorionic Gonadotropin and their Application to Two-Site Sandwich Radio Immunoassay", J. Immol. Meth. 74 (1984), 369–374.

Armstrong et al., "Use of a Highly Sensitive and Specific Immunoradiometric Assay for Detection of Human Chorionic Gonadotropin in Urine of Normal, Nonpregnant and Pregnant Individuals", J. Clin. Endocrinol. Met. 59(1984) 867–874.

Bellet et al, "Sensitive and Specific Assay for Human Chorionic Gonodotropin (hCG) Based on Anti-Peptide and Anti-hCG Monoclonol Antibodies: Construction and Clinical Implications", J. Clin. Endocrinol. Met. 63 (1986), 1319–1327.

Bellet et al, "A Monoclonal Antibody Against a Synthetic Peptide is Specific for the Free Native Human Chorionic Gonadofropin $\beta$-Subunit", Endocrinology 115(1984) 330–336.

Longhi et al, "Enzyme Immunoassay for Human Chorionic Gonadotropin Using Monoclonal Antibodies Elicited with a Synthetic Peptide", J. Immunol. Meth. 92(1986) 89–95.

Bidart et al., "Identification of Epitopes Associated with hCG and the BhCG Carboxyl Terminals by Monoclonal Antibodies Produced Against a Synthetic Peptide", J. Immunol. 134(1985), 457–464.

Caraux et al, "Non–Cross–Reactive Monoclonal Antibodies to Human Chorionic Gonadotropin Generated After Immunization with a Synthetic Peptide", J. Immunol. 134 (1985), 835–840.

Primary Examiner—Christine M. Nucker
Attorney, Agent, or Firm—Saidman, Sterne, Kessler & Goldstein

[57] ABSTRACT

A highly sensitive and specific monoclonal-immunoradiometric assay (M-IRMA) for hCG, using monoclonal antibodies (Mabs) directed against a 37-amino acid synthetic polypeptide analogous to the carboxyl terminus (CTP) of beta-hCG. Accordingly, in one embodiment, a method is described for the determination of human chorionic gonadotropin in a sample, which comprises:

(a) contacting said sample with a first capture monoclonal antibody and a second capture monoclonal antibody which are bound to a carrier, wherein said first and second capture antibodies are epitopically specific for distinct epitopes of the carboxy terminal region of the beta-subunit of human chorionic gonadotropin;

(b) incubating the components of step (a) for a period of time and under conditions sufficient to form an immune complex between said human chorionic gonadotropin, said first capture monoclonal antibody, said second capture monoclonal antibody and said carrier;

(c) adding to said carrier of step (b), a detectably labeled indicator monoclonal antibody, wherein said indicator monoclonal antibody is epitopically specific for the alpha-subunit of human chorionic gonadotropin;

(d) determining the detectably labeled indicator monoclonal antibody in said carrier or in liquid phase.

29 Claims, 5 Drawing Sheets

Ventrescreen hCG, Ventrex Laboratories, Inc., Portland, ME 04103.

Shimizu et al, "Choriganadotropin Measured by Use of Monoclonal Antibodies in a Two Site Immunoradiometric Assay", Clin. Chem. 28 (1982), 546–547.

Rugg et al, "Radial Partition Immunoassay Applied to Automated Quantification of Human Choriogonadotropin with Use of two Monoclonal Antibodies", Clin. Chem. 32 (1986), 1844–1848.

Tyrey, L., Sem. Oncol. 9:163–173 (1982).

Matsuura, S. et al., Endocrin. 104:396–401 (1979).

Ehrlich, P. H. et al., J. Immunol., 128: 2709–2713 (1982).

Berger, P. et al., Am. J. Reprod. Immunol., 5: 157–160.

Light, P. A. et al., Lancet 1: 1284 (1983).

Skelly, D. S., The Ligand Review, 3: 4 (1981).

Hussa, R. O., The Ligand Review, 3: 6–44 (1981).

Vaitukaitis, J. L., The Ligand Review, 3: 45–48 (1981).

Tandem-Visual hCG Pregnancy Test, Hybritech Inc., San Diego, CA 92121.

Pregnospia, Organon Diagnostics, West Orange, NJ 07052.

Neo-Pregnosticon Duoclon, Organon Diagnostics, West Orange, NJ 07052.

Star beta-hCG RIA, Syncor International Corp., Sylmar, CA 91342.

Pregnastick, Monoclonal Antibodies, Inc., Mountain View, CA 94043.

ModEL Serum hCG Assay, Monoclonal Antibodies, Inc., Mountain View, CA 94043.

ModEL Plus Urine hCG Assay, Monoclonal Antibodies, Inc. Mountain View, CA 94043.

Beta-Neocept, Organon Diagnostics, West Orange, NJ 07052.

IMMUNOMETRIC ASSAY FOR THE DETECTION OF HUMAN CHORIONIC GONADOTROPIN

The present invention was made utilizing funds of the United States Government. The U.S. government is therefore granted a royalty-free, non-exclusive, world wide, paid-up license in this invention.

BACKGROUND OF THE INVENTION

1. Field of the Invention

The present invention relates to an immunometric assay using monoclonal antibodies for the detection or determination of human chorionic gonadotropin.

2. Brief Description of the Background Art

Human chorionic gonadotropin (hCG) is a placental glycoprotein hormone composed of two non-identical alpha and beta subunits. Tyrey, L., *Semin. Oncol.* 9:163 (1982). The alpha subunit of hCG is virtually identical to the alpha subunits of thyroid-stimulating hormone (TSH), luteinizing hormone, (LH) and follicle-stimulating hormone (FSH). The unique biologic and immunologic reactivity of these hormones, however, is defined by their beta subunits, which are structurally different for each hormone. The 145 amino acid beta subunit (beta hCG) of hCG has over 80% homology with the beta subunit (beta LH) of LH. The single major structural difference between the beta subunits of these two hormones is the presence in beta hCG of an extra COOH-terminal extension (residues 115-145), which is absent from beta LH. Morgan, F. J. et al., *J. Biol. Chem.* 250: 5247 (1975). hCG and LH display similar immunoreactivity due, in part, to their extensive amino acid sequence homology. Bidart, J. et al., *J. Immunol.* 134 (1):457 (1985).

Because of these extensive chemical homologies between hCG and LH, specific detection of hCG is problematic. For example, both antisera and monoclonal antibodies (Mabs) elicited against hCG cross-react with LH. Tyrey, L., supra. Moreover, radioimmunoassays (RIAs) presently in clinical use cannot easily detect low levels of hCG (less than 0.5 ng/ml) without concentration of the biological sample. Borkowski, A. et al., *J. Clin. Endocriol. Metab.* 58:1171 (1984). These limitations have hampered studies on hCG production in healthy individuals. Borkowski, A. et al. supra; Borkowski, A. et al., *N. Engl. J. Med.* 301:298 (1979). Also, it is known that certain neoplasms secrete hCG. Thus, hCG can be used as a "marker" for diagnosing or monitoring treatment of some human neoplasms. Tyrey, L., supra. However, more sensitive assays for hCG are required to detect early recurrance following treatment for trophoblastic tumors.

To achieve better specificity and sensitivity in the immunologic recognition of hCG, several attempts have been made to produce antibodies directed against the unique beta-COOH-terminal structure of hCG (residues 115-145) by using as immunogens C-terminus peptides (CTP) of the hCG beta subunit or C-terminus synthetic peptide analogues. See, for example, Louvet, J.P. et al., *J. Clin. Endocrinol. Metab.* 39:1155 (1974); Matsuura, S. et al., *Endocrinol.* 104:396 (1979); Birken, S. et al., *Endocrinol.* 110:1555 (1982). Antisera and monoclonal antibodies thus produced were, however, of low affinity, and the sensitivity of the assays was poor or offered no advantages compared to antibodies raised against the entire hCG subunit. Birken, S. et al., "Immunochemical Recognition of Human Choriogonadotropin," in, Burchiel, S. W. et al., (Eds.) *Tumor Imaging*, Masson Publishing, U.S.A., Inc., New York, p. 41 (1982); Bellet, D. et al., *Endocrinol.* 115:330 (1984); Bidart, J.M. et al., *J. Immunol.* 134:457 (1985).

Thus, although several hCG immunoassays based on monoclonal anti-CTP antibodies recently have been described, Bidart, J.M. et al., supra; Caraux, J. et al., *J. Immunol.* 134:835 (1985), the sensitivity of these assays is similar to that obtained with antibodies raised against the intact hormone. Similarly, Canfield et al., PCT Publication No. 84/04598, disclose an hCG immunoassay utilizing a polyclonal antibody to the carboxy terminal peptide of the beta hCG subunit in conjunction with a Mab to the beta hCG subunit, which has the disadvantages associated with the use of polyclonal antibodies. A need, therefore, has continued to exist for a highly sensitive and specific assay for hCG.

SUMMARY OF THE INVENTION

The present invention arose out of the discovery that the sensitivity of total monoclonal sandwich assays for hCG is greatly increased when two antibodies epitopically specific for distinct epitopes of the carboxy terminal region of the beta-subunit of hCG are immobilized on a solid phase (i.e., two "capture" antibodies bound to the "carrier"), and, after washing to remove unbound material, a third detectably labelled antibody (i.e., "indicator" antibody) epitopically specific for the alpha-subunit of hCG is added.

In the invention, any one of the immobilized antibodies alone may have high, moderate or even low affinity for hCG when tested in a sandwich assay by itself, using the same or a different antibody in labelled soluble form. Greatly increased sensitivity, however, is brought about by the relationship between the binding of the combination of two different antibodies epitopically specific for distinct epitopes of the carboxy terminal region of the beta-subunit of hCG and the binding of the single antibody epitopically specific for the alpha-subunit of hCG in the liquid phase. This may be brought about by the "appearance" or "presentation" upon immobilization of the antigen on the solid phase via the antibodies of an additional epitope or epitopes. This "presentation" allows substantial binding of the soluble, detectably labelled antibody to the immobilized antigen.

This phenomenon dramatically increases the selectivity and sensitivity of the assay of the present invention, since it distinguishes over similar polyvalent antigens which already carry in their soluble state (i.e., while not bound to the solid phase via the antibodies) the additional epitopes needed to provide high binding to the soluble antibody. Very fine epitopic differences can be obtained with the present assay.

Thus, in one embodiment, the present invention provides an immunometric assay for the determination of human chorionic gonadotropin in a sample, which comprises:

(a) contacting said sample with a first capture monoclonal antibody and a second capture monoclonal antibody which are bound to a carrier, wherein said first and second capture monoclonal antibodies are epitopically specific for distinct epitopes of the carboxy terminal region of the beta-subunit of human chorionic gonadotropin;

(b) incubating the components of step (a) for a period of time and under conditions sufficient to form an immune complex between said human chorionic gonadotropin, said first capture monoclonal antibody, said second capture monoclonal antibody, and said carrier;

(c) adding to said carrier of step (b), a detectably labelled indicator monoclonal antibody, wherein said indicator monoclonal antibody is epitopically specific for the alpha-subunit of human chorionic gonadotropin; and (d) determining the detectably labelled indicator monoclonal antibody in said carrier or in liquid phase.

As an example, after screening, various different anti-CTP monoclonal antibodies and various combinations and permutations thereof, it was discovered that one specific combination of two capture antibodies epitopically specific for distinct epitopes of the carboxy terminal region of the beta-subunit of hCG, in combination with an indicator antibody epitopically specific for the alpha-subunit of hCG, in a total monoclonal immunometric assay of hCG, results in sensitivities heretofor unobtainable with prior art assays for hCG. A sandwich assay is carried out with this configuration.

The inventors postulated that the low affinity constants ($K_{asn}$) of monoclonal anti-CTP antibodies ($0.2-1.5\times 10^7$/M) utilized in previous experiments, Bidart, J. M. et al., supra, were mainly responsible for the limited sensitivity of assays employing these antibodies. In an attempt to develop better assays, five monoclonal anti-CTP antibodies (FB02, FB07, FB08, FB09, and FB12) with different affinities and directed against distinct antigenic determinents were produced to explore the interaction of these antibodies with beta hCG (see FIG. 1). It was found that enhanced binding (additive effect) may be obtained by using two antibodies directed against distinct and separate epitopes, and that a mixture of anti-peptide Mabs will, with high efficiency, capture a complex native glycoprotein on a solid phase support. The inventors succeeded in isolating one cell line (FB12) from 33 cell fusion experiments which produced a Mab having an affinity constant greater than $10^9$/M. This is in the same order of magnitude as that found with Mabs produced by immunization with native hCG or beta subunit. Bidart, J. M. et al., supra; Berger, P. et al., Am. J. Reprod. Immunol, 5:157 (1984).

Thus, in a specific embodiment of the invention, there is provided an immunometric assay for the determination of human chorionic gonadotropin in a sample as described above, wherein at least one of said first and second capture antibodies directed against distinct and separate epitopes on said carboxy terminal region on the beta-subunit of human chorionic gonadotropin has a $K_{asn}$ which is greater than the low $K_{asn}$ of monoclonal anti-CTP antibodies used previously by Bidart, J. M. et al., supra. For the purposes of the present invention, a "low" $K_{asn}$ is less than $1\times 10^8$/M. A $K_{asn}$ equal to or greater than $1\times 10^8$/M but less than $10^9$/M is "moderate." A monoclonal antibody having a $K_{asn}$ greater than $1\times 10^9$/M exhibits "high" affinity for hCG. Thus, while the advantages of the use of two capture antibodies epitopically specific for distinct epitopes of the carboxy terminal region of the beta-subunit of hCG according to the present invention are realized even where both of said antibodies are of low affinity, it is preferred that at least one of the capture monoclonal antibodies of the present invention have a $K_{asn}$ which is at least moderate, or, more preferably, high. The other capture monoclonal antibody can be of low, moderate or high affinity. Those of skill will of course recognize that gains in sensitivity may be realized where both capture antibodies are of moderate or high affinity. The advantage of the present invention, however, lies in the discovery that utilizing as capture antibodies two monoclonal antibodies of distinct epitopic specificity of the COOH terminal region of the Beta-subunit of hCG results in a surprising increase in assay sensitivity that would not be expected given the affinities of the individual capture antibodies for hCG.

Hapten inhibition experiments provided evidence that FB12 recognized an antigenic determinant (epitope) localized on or about residues 110–116 of CTP, since the 110–116 sub-peptide produced 100% inhibition of antibody binding. The panel of subpeptides used in these experiments suggests that FB12 defines an epitope located on a peptide as short as 7 amino acid residues. The same panel did not permit the localization of antigenic determinants by the other four Mabs to a 7 amino acid sequence. Antibodies derived from cell lines FB08 and FB09 appear to bind CTP between residues 134–145. It is likely that the epitope recognized by these antibodies is located primarily on the 134–139 region, since subpeptide 139–145 does not inhibit antibody binding.

To detect hCG, a monoclonal anti-hCG antibody derived from cell line HT 13 that recognized an epitope on the alpha subunit of glycoprotein hormone was used as a radiolabelled indicator antibody. Labelled antibody binding experiments performed with ($^{125}$I)HT 13 demonstrated that an enhancement of the binding (synergistic effect) was obtained by using FB09 and FB12 as capture antibodies. Indeed, binding of ($^{125}$I)HT 13 to hCG (10 ng/ml) linked to a mixture of FB09 and FB12 is about 5 fold higher than the sum of binding exibited by hCG linked to each antibody alone.

Surprisingly, this monoclonal-immunoradiometric assay (M-IRMA) exhibited a very high sensitivity for hCG and was capable of detecting less than 50 pg/ml. Moreover, this assay was specific for hCG. No cross reactivity was observed with human LH at a concentration of 1,000 ng/ml. The M-IRMA does not detect the free beta hCG subunit due to the selection of HT 13 as a tracer; HT 13 binds only to the alpha subunit of the glycoprotein hormone.

Thus, in another embodiment of the invention, there is provided an immunometric assay for the determination of human chorionic gonadotropin in a sample as described above, wherein said first capture antibody is derived from cell line FB12, said second capture antibody is derived from cell line FB09, and said indicator antibody in HT 13.

Signal to noise ratio (S/N) is defined as CPM bound in experimental samples divided by the mean of negative controls. Left side: hCG, 1 ng/ml. Right side: hCG, 10 ng/ml.

Figure 3:
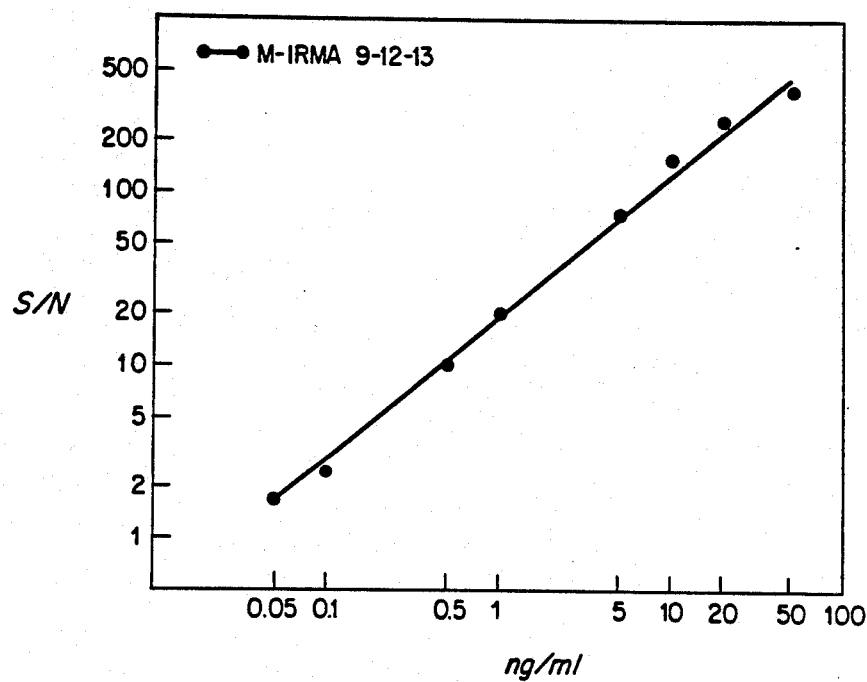

FIG. 3 shows a standard curve for a monoclonal immunoradiometric assay for hCG based on FB09 and FB12 as capture antibodies and ($^{125}$I) HT 13 as the radio labelled indicator antibody (M-IRMA 9-12-13).

Figure 4:
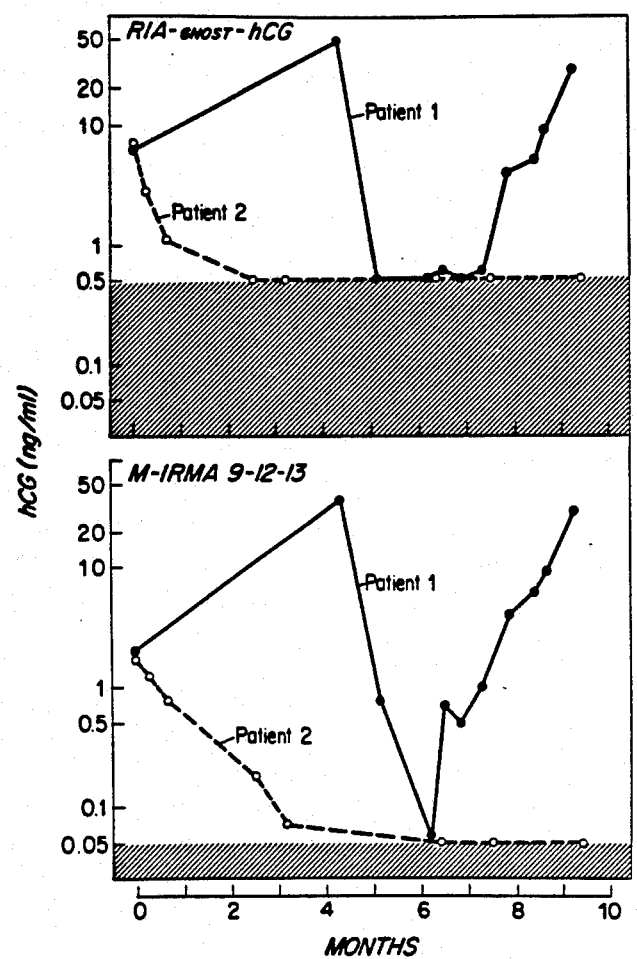

FIG. 4 shows a serial study of two patients using a commercial immunoradiometric assay (RIA-GNOST hCG) based on a monoclonal anti-beta hCG antibody (top) and an assay (M-IRMA 9-12-13) based on antipeptide antibodies (bottom). Patient 1: testicular tumor. Patient 2: gestational trophoblastic tumor. Lower limit of sensitivity of each assay is indicated by shaded area.

Figure 5:
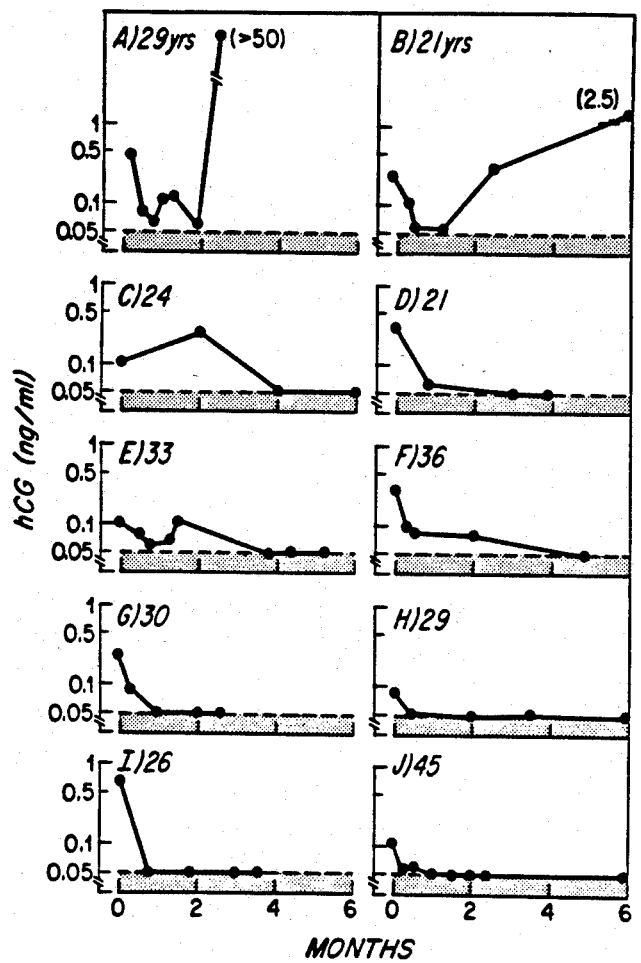

FIG. 5 shows hCG levels as determined by antipeptide based M-IRMA in the sera of 10 patients that had undetectable hCG levels by commercial immunoradiometric assay (CM-IRMA) except in two instances (Patient A: hCG greater than 50 ng/ml; patient B: hCG=2.5 ng/ml). Patient A, B, C, D, F, H, I and J were followed for a gestational trophoblastic tumor and patient E was followed for an ovarian tumor.

BRIEF DESCRIPTION OF THE PREFERRED EMBODIMENTS

By the term "immunometric assay" or "sandwich immunoassay," it is meant to include simultaneous sandwich, forward sandwich and reverse sandwich immunoassays. These terms are well understood by those skilled in the art.

In a forward sandwich immunoassay, the sample is first incubated with a solid phase immunoadsorbent/absorbent containing the two different monoclonal capture antibodies against hCG. Incubation is continued for a period of time sufficient to allow the hCG on/in the sample to bind to the immobilized antibodies in the solid phase. After the first incubation, the solid phase immunoabsorbent is separated from the incubation mixture and washed to remove excess hCG and other interfering substances, such as non-specific binding proteins, which also may be present in the sample. Solid phase immunoabsorbent containing hCG bound to the immobilized antibodies is subsequently incubated for a second time with soluble labelled indicator antibody. After the second incubation, another wash is performed to remove unbound labelled indicator antibody from the solid phase immunoabsorbent and removing non-specifically bound labelled antibody. Labelled antibody bound to the solid phase immunoabsorbent is then detected and the amount of labelled antibody detected serves as a direct measure of the amount of hCG present in the original sample. Alternatively, labelled antibody which is not associated with the immunoabsorbent complex can also be detected, in which case the measure is in inverse proportion to the amount of hCG present in the sample. Forward sandwich assays are described, for example, in U.S. Pat. Nos. 3,867,517; 4,012,294 and 4,376,110.

In carrying out forward immunometric assays, the process comprises, in more detail:

(a) first forming a mixture of the sample with the solid phase bound antibodies and incubating the mixture for a time and under conditions sufficient to allow hCG in the sample to bind to the solid phase bound antibodies;

(b) adding to the mixture after said incubation of step (a) the detectably labelled antibody or antibodies and incubating the new resulting mixture for a time and under conditions sufficient to allow the labelled antibody to bind to the solid phase immunoabsorbent;

(c) separating the solid phase immunoabsorbent from the mixture after the incubation in step (b); and (d) detecting either the labelled antibody or antibodies bound to the solid phase immunoabsorbent or detecting the antibody not associated therewith.

In a reverse sandwich assay, the sample is initially incubated with labelled indicator antibody, after which the solid phase immunoabsorbent containing the two immobilized capture antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110.

In carrying out reverse immunometric assays, the process comprises, in more detail:

(a) first forming a mixture of the sample with the soluble detectably labelled indicator antibody for a time and under conditions sufficient to allow hCG in the sample to bind to the labelled indicator antibody;

(b) adding to the mixture after the incubation of step (a) the solid phase-bound antibodies and incubating the new resulting mixture for a time and under conditions sufficient to allow hCG bound to the labelled antibody to bind to the solid phase antibodies;

(c) separating the solid phase immunoabsorbent from the incubation mixture after the incubation in step (b); and (d) detecting either the labelled antibody bound to the solid phase immunoabsorbent or detecting the labelled antibody not associated therewith.

In a simultaneous sandwich assay, the sample, the immunoabsorbent having the two immobilized capture antibodies thereon and labelled soluble indicator antibody are incubated simultaneously in one incubation step. The simultaneous assay requires only a single incubation and has a lack of washing steps. This type of assay brings about ease of handling, homogeneity, reproducibility, linearity of the assays and high precision. The sample containing hCG, solid phase immunoabsorbent with immobilized capture antibodies and labelled soluble indicator antibody are incubated under conditions and for a period of time sufficient to allow hCG to bind to the immobilized capture antibodies and to the soluble indicator antibody. In general, it is desirable to provide incubation conditions sufficient to bind as much hCG as possible, since this maximizes the binding of labelled antibody to the solid phase, thereby increasing the signal. Typical incubation times range from 2 to 24 hours. Typical incubation temperatures range from 20° C. to 45° C. Those of skill in the art will appreciate that incubation conditions may be varied as a routine matter in optimizing a given assay system.

Soluble labelled indicator antibody typically binds to hCG more rapidly than immobilized capture antibodies, since the former is in solution whereas the latter are bound to the solid phase support. Because of this, labelled indicator antibody may be employed in a lower concentration than immobilized capture antibodies, and it is also preferable to employ a high specific activity for labelled indicator antibody. For example, labelled indicator antibody might be employed at a concentration of about 1-50 ng/per assay, whereas immobilized capture antibodies might have a concentration of 10-500 ng/per assay per antibody. The labelled indicator antibody might have a specific activity with, for instance, one radioiodine per molecule, or as high as two or more radioiodines per molecule of antibody.

Of course, the specific concentrations of labelled and immobilized antibodies, the temperatures and time of incubation as well as other such assay conditions can be varied, depending on various factors including the concentration of antigen in the sample, the nature of the sample, and the like. Those skilled in the art will be able to determine operative and optimal assay conditions for each determination by employing routine experimentation.

After the single incubation period, the solid phase immunoabsorbent is removed from the incubation mixture. This can be accomplished by any of the known separation techniques, such as sedimentation and centrifugation. A washing step is not required prior to detection of bound labelled antibody. Detection can be performed by a scintillation counter, for example, if the label is a radioactive gamma-emitter, or by a fluorometer, for example, if the label is a fluorescent material. In the case of an enzyme label, the detection can be done by colorimetric methods employing a substrate for the enzyme.

In carrying out the simultaneous immunometric assay on a sample containing hCG the process comprises, in more detail:

(a) simultaneously forming a mixture comprising the sample, together with the solid phase-bound capture antibodies and the soluble labelled indicator antibody;

(b) incubating the mixture formed in step (a) for a time and under conditions sufficient to allow antigen in the sample to bind to both immobilized and labelled antibodies;

(c) separating the solid phase immunoabsorbent from the incubation mixture after the incubation; and (d) detecting either labelled capture antibody bound to the solid phase immunoabsorbent or detecting labelled capture antibody not associated therewith.

Other such steps as washing, stirring, shaking, filtering and the like may of course be added to the assays, as is the custom or necessity for any particular situation.

In the preferred mode for performing the hCG assay it is important that certain "blockers" by present in the incubation medium (usually added with the labelled soluble antibody). The blockers are added to assure that non-specific proteins, proteases, or human antibodies to mouse immunoglobulins present in the experimental sample do not cross-link or destroy the monoclonal antibodies on the solid phase support, or the radiolabelled indicator antibody, to yield false positive or false negative results. The selection of blockers therefore adds substantially to the specificity of the assays described in the present invention. It has been found that a number of non-relevant (i.e. non specific) monoclonal antibodies of the same class or subclass (isotype) as those used in the assays (e.g. $IgG_1$, $IgG_{2a}$, IgM, etc.) can be used as blockers. The concentration of the blockers (normally 1-100 ug/ul) is important, in order to maintain the proper sensitivity yet inhibit any unwanted interference by mutually occurring cross reactive proteins in human serum. Preferred for the purposes of the present invention is the use of a non-relevant monoclonal IgG blocker at a concentration of 20 ug/100 ul. In addition, the buffer system containing the blockers needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01-10 ug/ml) to the buffer which contains the blockers.

There are many solid phase immunoabsorbents which have been employed and which can be used in the present invention. Well known immunoabsorbents include beads formed from glass, polystyrene, polypropylene, dextran, nylon and other materials; tubes formed from or coated with such materials, and the like. The immobilized antibodies can be either covalently or physically bound to the solid phase immunoabsorbent, by techniques such as covalent bonding via an amide or ester linkage, or by absorption. It is important that the two immobilized capture antibodies be bound to the same solid phase since close proximity is important. This can be readily achieved by either simultaneous or sequential binding of each antibody on the same solid phase. Those skilled in the art will know many other suitable solid phase immunoabsorbents and methods for immobilizing antibodies thereon, or will be able to ascertain such, using no more than routine experimentation.

The monoclonal antibody which remains in the soluble state, and is used as the detectably labelled indicator antibody, can be a single antibody or a mixture thereof. The soluble antibody can be labelled with any detectable label, such as a radiolabel, a fluorescent label, an enzyme label, a free radical label or a bacteriophage label. Most commonly, the label is a radiolabel (radioimmunoassay) or an enzyme label (enzyme immunoassay). The more common radiolabels are $^{125}I$, $^{131}I$, $^3H$ and $^{14}C$. Among the common enzyme labels are horseradish peroxidase, alkaline phosphatase, beta-D-galactosidase, glucose oxidase and glucoamylase. Among the fluorescent materials are, for example, fluorescein isothiocyanate, and rhodamine.

Any animal sample containing a detectable yet unknown amount of hCG can be used. Such sample is normally from a human and may be liquid (such as, for example, urine, saliva, blood, serum and the like), or solid or semi-solid (tissues, feces, and the like).

The term "epitope" as used in this invention is meant to include any antigenic determinant of an antigen responsible for specific interaction with antibody molecules elicited by the same or related antigen. Antigenic determinants usually consist of chemically active surface groupings of molecules such as amino acids or sugar side chains. The epitopes have specific three dimensional structural characteristics as well as specific electronic characteristics.

Any monoclonal antibodies with low, moderate of high affinity can be used, such as IgG, IgE, IgM, and the like. Preferred among these are IgM and IgG, especially those of moderate affinity (e.g., $\geq 10^8 M^{-1}$), and more especially those of high affinity (e.g., $\geq 10^9 M^{-1}$).

The method of the present invention requires selection of at least two different capture antibodies with affinity towards two distinct epitopes, on the carboxy terminal region of the beta-subunit of hCG, which may then be immobilized. Selection of an antibody combination can normally be carried out by choosing each antibody from a different cell line.

Any variation of the sandwich assays, as long as it utilizes the combination of antibodies described, can be used in the present invention. Any automated technique which utilizes a sandwich immunoassay or variations thereof can of course be applied to the basic technique of the present invention. For example, such a technique is described in Goldie et al. U.S. Pat. No. 4,251,360.

In addition, the materials for use in the assay of the invention are ideally suited for the preparation of a kit. Such a kit may comprise a carrier means being compartmentalized to receive in close confinement one or more container means such as vials, test tubes and the like, each of said container means comprising one of the separate elements to be used in the method.

For example, one of said container means may comprise immunoabsorbent-bound different monoclonal capture antibodies. These antibodies may be bound to a separate solid phase immunoabsorbent or directly to the inner walls of a container. A second container may comprise soluble detectably labelled antibody in lyophilized form or in solution.

The carrier may also contain, in addition, a plurality of containers each of which comprises different, predetermined known amounts of antigen. These latter containers can then be used to prepare a standard curve into which can be interpolated the results obtained from the sample containing the unknown amount of antigen.

In using a simultaneous assay, for example, all a user has to do is add, to the first container, a premeasured amount of an animal sample containing the measurable, yet unknown amount of hCG in a buffer and simultaneously add the contents of the labelled antibody present in the second container into the first container. Alternatively, all components are added to a separate container. After an appropriate time for incubation, solid phase is separated from the supernatant fluid, and the solid phase or the supernatant fluid are detected, as by radioactive counting or addition of any enzyme substrate, and color development.

Methods of preparing monoclonal antibodies and of determining their specificity and affinity for antigens generally are well-known in the art. See, e.g., Campbell, A. M., "Monoclonal Antibody Technology: Production and Characterization of Rodent and Human Hybridomas," in, R. H. Burdon et al., eds, *Laboratory Techniques in Biochemistry and Molecular Biology*, Elsevier, Amsterdam (1984). Preferred monoclonal capture antibodies for the purposes of the present invention are those produced by the cell lines FB12, FB09 and FB08. The cell line FB12 is deposited in the Collection Nationale de Cultures de Microorganisms (C.N.C.M.) of the Institut Pasteur as of Oct. 14, 1986, designated I-613. The cell line FB09 is deposited in the C.N.C.M. of the Institut Pasteur as of Oct. 14, 1986, designated I-612. A preferred indicator antibody for the purposes of the present invention is that produced by the cell line HT 13. The cell line HT 13 is deposited in the C.N.C.M. of the Institut Pasteur as of Oct. 3, 1985, designated I-490. Preparation and isolation of other appropriate antibodies and cells can be obtained by, for example, the methods described in Kennett, R. H., et al., *Monoclonal Antibodies. Hybridomas: A New Dimension in Biological Analyses*, Plenum Press, New York and London, 1982, especially pp. 363–418.

Having now generally described this invention, the same will be better understood by reference to certain specific examples which are incorporated herein for purposes of illustration only and are not intended to be limiting of the invention unless specified.

EXAMPLE

Anti-CTP Based M-IRMA for hCG

MATERIALS AND METHODS:

Synthetic peptides and peptide-carrier conjugate:

A peptide (CTP) corresponding to the COOH-terminal segment of beta hCG (residues 109–145 as defined by Morgan, F. J. et al., *J. Biol. Chem.* 250:5247 (1975), and various subpeptides thereof corresponding to shorter fragments (subpeptides 110–116, 121–145, 127–138, 134–145, 139–145) were synthesized by a solid phase method on a benzyhydrylamine resin, Merrifield, R. B., *J. Am. Chem. Soc.* 85:2149 (1963). The cleavage of the final peptide from the polymer support was carried out by hydrofluoric acid in the presence of anisole and resulted in a carboxamide group at the C-terminus. Cysteine 110 was protected with the hydrofluoric acid-resistant acetamidomethyl group. After gel filtration on Biogel P 6 (Bio-Rad, Richmont, Calif.) and ion exchange chromatography on CM 52 (Whatman, Clifton, N.J.), the peptides were found to be homogenous, as shown by reverse high pressure liquid chromatography and thin layer chromatography analysis. Amino acid analysis and/or peptide sequence analysis by Fast Atom Bombardment, Morris, H. R. et al., *Biochem. Biophys. Res. Comm.* 101:623 (1981), demonstrated that the peptides had the expected amino acid composition and sequence. The 109–145 synthetic peptide was conjugated to tetanus toxoid (TT) with glutaraldehyde used as the coupling agent, according to a previously described method, Audibert, F. M. et al., *Proc. Natl. Acad. Sci. USA* 79:5042 (1982).

Preparation of monoclonal antibodies:

The immunizations were performed on 25 six-week-old BALB/c and 9 high responder strain (HR) mice, Biozzi, G. et al., *J. Exp. Med.* 132:752 (1970). One HR mouse was injected with hCG (Boehringer Mannheim, West Germany). Other animals were injected with the CTP-TT conjugate according to several different immunization schedules that varied the concentration of immunogens and the interval between the primary immunization and the secondary boost, Bellet, S. et al., *Endocrinology* 115:330 (1984); Bidart, J. M. et al., *J. Immunol.* 134:457 (1985). The details of the protocols leading to the production of monoclonal antibody FB02 have been described, Bidart, J. M. et al., supra. Other antibodies used in this study were obtained after an initial immunization with either hCG (10 ug) or CTP-TT (100 ug) s.c. in Freund's complete adjuvant. Three to seven months after this injection, the same dose of immunogen was given 9 days (s.c. in Freund's incomplete adjuvant) and 3 days (i.v.) before fusion. Spleen cells were fused with Sp2/0 -Ag 14 or NS1 mouse myeloma cells as previously described, Bidart, J. M. et al. supra. After 2 weeks of culture, supernatants were tested for production of either anti-hCG or anti-beta hCG antibodies by a radioimmunoassay. Briefly, the RIA was performed by incubating at 4° C., ($^{125}$I) hCG ($2 \times 10^4$ cpm, specific activity 200 uCi/ug; 1 Ci=$3.7 \times 10^{10}$ becquerels, Commissariat a l'Energie Atomique, Saclay, France) with 100 ul of culture supernatant for 16 h. The antigen-antibody complex was precipitated by 1 ml of 20% PEG 6000 in the presence of 100 ul normal human serum diluted 1:3 in PBS pH 7.4. After resuspension and subsequent centrifugation, the radioactivity of the pellet was determined in a gamma well counter. Cells from positive wells were cloned twice by limiting dilution and ascites fluids were produced by i.p. inoculation of nude mice with $5 \times 10^5$ hybridoma cells. The isotypes of monoclonal antibodies were determined by either dotimmunobinding assay, Beyer, C. F. *J. Immunol. Methods* 67:79 (1984), or a double antibody RIA as previously described, Bidart, J. M. et al., supra. Immunoglobulin G (IgG) was purified (2mg/ml) from mouse ascites fluids using 50% ammonium sulfate precipitation and protein A affinity chromatography.

Measurement of monoclonal antibody affinity constants:

The affinity constant (Kasn) of each anti-CTP monoclonal antibody was determined by measuring the binding of ($^{125}$I) beta hCG in the presence of increasing amounts of purified unlabeled antibody. Briefly, ($^{125}$I) beta hCG ($2 \times 10^4$ cpm) was incubated with purified antibodies (2 to $500 \times 10^{-8}$ M) in PBS for 16 h at 4° C. The immune complex was precipitated by PEG according to previously described experimental conditions and the radioactivity bound was measured. The affinity constants were then calculated from the RIA binding results as reported by Van Heyningen, V. et al., *J. Immunol. Methods* 62:147 (1983).

Affinity constants of anti-hCG antibodies for hCG or alpha hCG with ($^{125}$I) hCG or alpha hCG (Batch CR-123 generously supplied by the Center for Population Research, NICHHD, National Institutes of Health) and radiolabelled using the Iodogen method, Fraker, P.J. et al., *Biochem. Biophys. Res. Commun.* 80:849 (1978). Briefly, monoclonal antibody was incubated with radiolabeled hCG or alpha subunit in the presence of increasing levels of unlabelled hormone or subunit and Kasn was determined from binding data by Scatchard plot analysis.

Monoclonal antibody specificity: The RIA described for screening hybridomas was performed with ($^{125}$I)hLH, ($^{125}$I)hFSH or ($^{125}$I)hTSH (Commissariat a l'Energie Atomique) in an attempt to evaluate the potential cross reactivity of each antibody with the other glycoprotein hormones.

To localize the epitopes recognized by each antibody, the reaction of a monoclonal antibody with a defined subpeptide sequence was determined by a competitive inhibition assay. In brief, monoclonal antibody was incubated with various subpeptides followed by measurement of the residual anti-CTP activity with a solid phase enzyme linked immunosorbent assay (ELISA) as described previously, Bidart, J.M. et al., supra.

Antigen binding studies: Binding of beta hCG to various combination of anti-CTP monoclonal antibodies was studied by RIA as follows. Polystyrene beads (outer diameter, 0.64 cm, Precision Plastic Ball, Chicago, IL) were coated with a single monoclonal antibody or a mixture of different antibodies (ascites fluids diluted 1:500 in PBS pH 7.5) for 16 h at 20 C. Next 100 ul ($^{125}$I) beta hCG ($2.3 \times 10^4$ cpm) diluted in 0.01 M PMS, pH 7.4 (200 ul) were added to precoated solid phase-linked monoclonal antibody for 4 h at 37C. After washing, the radioactivity was determined. A monoclonal antibody directed to an irrelevant antigen (anti alpha-fetoprotein designated as AF01) was used as negative control at the same dilution as the anti-CTP antibodies.

Labeled antibody binding studies: In an attempt to determine the binding capacity of a radiolabeled anti-hCG monoclonal antibody to hCG bound to a solid phase support by anti-CTP monoclonal antibodies, multisite immunoradiometric assays were developed. Purified monoclonal antibody HT 13 was labeled with ($^{125}$I) (Commissariat a l'Energie Antomique, Saclay, France) using the Iodogen method, Fraker, P. J. et al., supra. Monoclonal anti-CTP antibodies FB09 and/or FB12 precoated on a solid phase support as previously described were incubated for 2 h at 20C with either 1 ng/ml or 10 ng/ml hCG (CR 123, NIH) in 200 ul of normal human serum (NHS). Beads were extensively washed with deionized water, followed by the addition of 200 ul of ($^{125}$I) HT 13 (100,000 cpm, specific activity 10–12 uci/ug) in 0.01 M PBS pH 7.4 containing 50% fetal calf serum. After incubation for 1 hr at 20C followed by a washing step, the radioactivity count (cpm) was determined.

Anti-CTP based M-IRMA for hCG: The antigen-antibody binding studies described above were important components for the construction of a multisite monoclonal immunoradiometric assay (M-IRMA). This "forward-sandwich" assay uses a mixture of FB09 and FB12 anti-CTP antibodies as "capture" antibodies on the solid phase support and ($^{125}$I) HT 13 serves as the radiolabelled indicator antibody. In brief, polystyrene beads were coated at room temperature with FB09 and FB12 (50% v/v of ascites fluids diluted 1:500 in PBS pH 7.5). hCG-positive standards or serum samples (200 ul) were added to the anti-CTP-coated beads. After an incubation for 2h at 20C followed by extensive washing with deionized water, 100,000 cpm of ($^{125}$I) HT 13 (specific activity: 10–12 uCi/ug) in 200 ul of buffer (0.01 M PBS pH 7.4 containing 50% fetal calf serum and 40 ug/100 ul of a nonspecific mouse IgG) were added. The reaction mixture was then incubated for 1 h at 20C followed by a washing step and the radioactivity bound determined. Assay standards consisted of hCG (CR 123, NIH) diluted in pooled normal serum previously shown to lack hCG binding activity. Potential cross-reactivity with human luteinizing hormone was evaluated with purified hLH (hLH-1-3, NIH). The sensitivity of the assay was defined by the least detectable dose, i.e., the hCG concentration resulting in an increase in counts per min (cpm) bound that was seven standard deviation (SD) units higher than the mean of the binding in ten replicate zero calibrator (pooled normal serum).

In selected patients, we compared the binding activities of M-IRMA using anti-CTP antibodies to a commercial immunoradiometric assay (CM-IRMA) based on a monoclonal anti-beta hCG antibody. Both M-IRMAs employ a monoclonal antibody directed against alpha hCG subunit as the radiolabelled indicator. We used the RIA-GNOST hCG commercial system (Behring, Marburg, West Germany). This "forward sandwich" assay was performed according to the manufacturer's instructions with two incubation periods of 30 min and 1 h, respectively. The sensitivity was found to be 0.5 ng/ml.

Subjects: From a serum bank at Institut Gustave-Roussy, we selected 229 sera from apparently healthy blood donors (179 males, 50 non-pregnant females and 76 sera from patients with hCG-producing tumors (8 hydatidiform moles, 2 gestational choriocarcinoma, 1 ovarian and 1 testicular carcinoma)). Sera from twelve patients were collected at different times over a 3 to 9 month period. All sera used in the present investigation had been stored at $-20°$ C. prior to analysis.

RESULTS:

Selection and characterization of monoclonal anti-CTP antibodies: Of the initial 3,000 hybridoma clones produced from 33 cell fusion experiments performed with mice immunized with CTP-TT, only 160 culture supernatants were positive for binding activity to ($^{125}$I) beta hCG. It was noteworthy that only 9 anti-beta hCG antibody secreting clones were obtained from the BALB/c fusions, whereas the other 151 were generated from the HR strain of mice. Initially, 15 hybrids producing antibodies capable of binding more than 10% of the ($^{125}$I) beta hCG were cloned under limiting dilution conditions. All antibodies were found to be of low affinity for beta hCG (Kasn of approximately $10^7$ M$^{-1}$) except one designated FB12 with a high Kasn of $2.3 \times 10^9$ M$^{-1}$.

Figure 1:
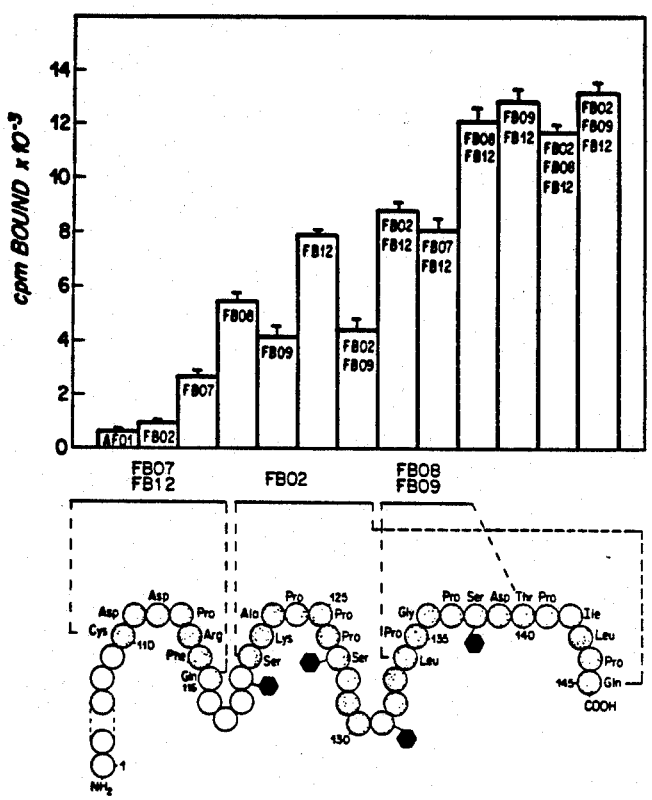
FIG. 1 shows the binding of ($^{125}$I) beta hCG to various combinations of monoclonal anti-CTP antibodies. Mean values ±SD (from 10 experiments) are shown. Also shown in FIG. 1 are the antigenic determinants of the antibodies derived from cell lines FB02, FB07, FB08, FB09 and FB12.

The antigenic region recognized by each of the antibodies was identified by competitive inhibition experiments with subpeptides of defined sequences. For these experiments the binding of monoclonal antibody to synthetic peptide linked to a solid-phase support was tested for inhibition by a related but shorter amino acid sequence. It was first necessary to determine the molar concentration of the 109-145 peptide required to give 100% inhibition of antibody binding. A total inhibition was achieved with $5 \times 10^{-5}$ M and this concentration was used in all subsequent competitive inhibition assays for either the 109-145 peptide or related smaller subpeptides. Epitope binding regions were deduced from inhibition profiles observed for each antibody. Because 100% inhibition of both FB07 and FB12 binding was obtained with subpeptide 110-116, whereas no inhibition was observed with other fragments of CTP, we were led to believe that these antibodies recognized an epitope located between amino acid residues 110 and 116. These results demonstrate that region 110-116 is accessible to antibody binding in hCG, since both FB07 and FB12 are directed against this CTP portion and bind to the native glycoprotein hormone. Inhibition experiments performed with the two other antibodies designated FB08 and FB09 have shown that 100% inhibition was obtained with subpeptides 121-145 and 134-145 whereas no inhibition was observed with other fragments including the 139-145 subpeptide. These results suggest that both antibodies identify an antigenic determinant present on 134-145 portion of the peptide molecule and it appears likely that the epitope resides between amino acid residues 134 and 139. The antigenic region recognized by FB02 was localized to the 121-145 portion of the peptide. Inhibition experiments with antibody FB02 demonstrated that subpeptide 121-145 was the only fragment leading to 100% inhibition whereas no inhibition was observed with sequences 121-132, 127-138 or 139-145 of the 121-145. Thus the antigenic region recognized by FB02 is situated between amino acids 121 and 145.

hCG to anti-CTP antibodies linked alone or in combination on a solid phase support. Results presented in FIG. 1 show that the binding was dependent in large part on the affinity of the antibody. For example, FB02 has the lowest binding activity for ($^{125}$I) beta hCG (1%) whereas FB12 bound 31% of the added radiolabeled subunit. It is also noteworthy that the combination of two monoclonal antibodies, namely FB07 and FB12, both of which identify the same epitope, does not lead to enhanced binding of beta hCG. In contrast, a combination of two antibodies, each of which is directed against a distinct and separate epitope on CTP, exhibits enhanced beta hCG binding activity. For example, the combination FB09 and FB12 exhibited a binding activity of 53% and this represents the sum of binding displayed by each antibody alone (additive effect).

Figure 2:
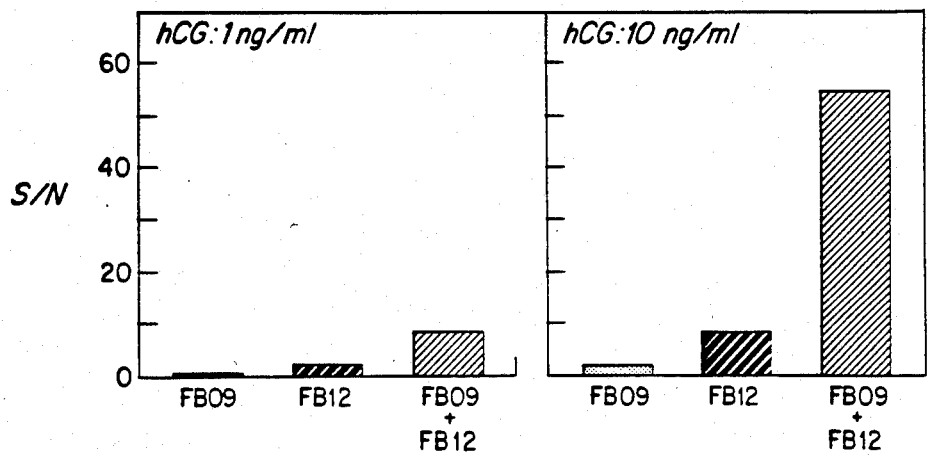
FIG. 2 shows the binding of ($^{125}$I) HT 13 to hCG immobilized on a solid phase support by anti-CTP antibodies FB09 and FB12 either alone or in combination.

Labeled antibody binding studies: To construct an immunoradiometric assay for native hCG, we determined the capacity of a labeled anti-hCG antibody to bind hCG linked on a solid phase support through anti-CTP antibodies. We used monoclonal antibody designated as HT 13. Antibody HT 13, of IgG$_1$ subclass, recognizes an epitope located on the alpha subunit and has calculated affinity constants for alpha hCG and hCG of $1.3 \times 10^{10}$ and $3 \times 10^{10}$ M$^{-1}$, respectively. Labeled antibody binding studies with ($^{125}$I) HT 13 were performed as described. On the basis of antigen binding studies, we used FB09 and FB12 either alone or in combination to "capture" hCG on polystyrene beads. Results are presented in FIG. 2 where binding activities are expressed as signal to noise ration (S/N) defined as cpm bound in experimental samples divided by the mean cpm of negative controls. At low dose of hCG (1 ng/ml) no significant binding was observed to hCG linked by FB09 whereas a S/N of 2 was measured with FB12. By using both FB09 and FB12 (50% v/v) on the solid phase, a synergistic effect was noted with a S/N of 9. This synergistic effect was also found at a high concentration of hCG (10 ng/ml) with S/N of 2, 9 and 54, respectively for FB09, FB12 and a mixture of the two anti-CTP antibodies.

Multisite monoclonal immunoradiometric assay for hCG: A "forward sandwich" multisite monoclonal

TABLE 1

| HYBRIDOMA CLONE | Characteristics of monoclonal antibodies produced against the 109-145 peptide (CTP) | | | | | | | EPITOPE BINDING REGION |
|---|---|---|---|---|---|---|---|---|
| | Kasn* | INHIBITION OF BINDING % | | | | | | |
| | | 110-116 | 121-132 | 121-145 | 127-138 | 134-145 | 139-145 | |
| FB02 | $0.2 \times 10^7$ | 0 | 0 | 100 | 0 | 0 | 0 | 121-145 |
| FB07 | $0.5 \times 10^7$ | 100 | 0 | 0 | 0 | 0 | 0 | 110-116 |
| FB08 | $2.9 \times 10^7$ | 0 | 0 | 100 | 0 | 100 | 0 | 134-145 (134-139) |
| FB09 | $0.3 \times 10^7$ | 0 | 0 | 100 | 0 | 100 | 0 | 134-145 (134-139) |
| FB12 | $2.3 \times 10^7$ | 100 | 0 | 0 | 0 | 0 | 0 | 110-116 |

*Kasn = affinity constant measured for ($^{125}$I) beta hCG and expressed in liters/mole. Parentheses indicate amino acid residues more likely to contain the epitope binding region.

Among the antibodies produced by cloned hybrids, a panel of five monoclonal anti-CTP antibodies was studied. These antibodies have different affinities and binding specificities to distinct regions on the synthetic peptide (Table 1). These antibodies were all of the IgG$_1$ subclass and recognized glycoproteins with CTP specific structure, namely beta hCG or hCG; antipeptide antibodies did not cross react with other glycoprotein hormones such as hLH, hFSH or hTSH which lack the COOH terminal region of the beta-subunit of hCG.

Interaction of monoclonal anti-CTP antibodies with beta hCG: We investigated the binding of ($^{125}$I) beta immunoradiometric assay (M-IRMA) based on a mixture of FB09 and FB12 on the solid phase and ($^{125}$I) HT 13 as indicator antibody was developed. The sensitivity and the specificity of this assay for detection of intact hCG glycoprotein hormone were assessed. The sensitivity of the "two-step" assay determined as described in methods was found to be below 0.05 ng/ml after two incubation periods of 2 h and 1 h, respectively.

Standard curves performed with hCG and hLH demonstrated specificity for hCG since no cross reactivity with hLH was observed at concentrations varying from 0.05–1000 ng/ml (S/N<2.0). A hCG standard curve is shown in FIG. 3. The slope of the dose-responsive curve for hCG in serum was 0.83. Intra assay and interassay variances were established using pooled normal serum to which known concentrations of hCG were added. Rodbard, D. et al., *Clin. Chem.* 20:1255 (1974).

At a level of 0.1 ng hCG/ml serum, the coefficients of intraassay (n=40) and interassay (n=15) variance were 20.7% and 21.8%, respectively. At a value of 1 ng hCG/ml serum, the coefficients of intraassay (n=20) and interassay (n=15) variance were 2.9% and 7.9%, respectively. We performed recovery studies in which serum derived from normal controls were augmented with small amounts of hCG and subsequently analyzed in duplicate by M-IRMA. The recoveries of 0.5 (n=3), and 5 ng hCG/ml serum (n=3) were 104+17% (±SD) and 103±17% respectively.

TABLE II

Serum hCG levels as measured by M-IRMA in 229 healthy blood donors

| | MALES | | FEMALES | |
|---|---|---|---|---|
| AGE | TOTAL NUMBER OF SUBJECTS | NUMBER OF SUBJECTS POSITIVE* | TOTAL NUMBER OF SUBJECTS | NUMBER OF SUBJECTS POSITIVE* |
| 21–30 | 69 | 0 | 23 | 1 |
| 31–40 | 48 | 1 | 9 | 0 |
| 41–50 | 38 | 0 | 11 | 1 |
| 51–60 | 24 | 1 | 7 | 6 |
| | 179 | 2 | 50 | 8 |

*hCG > 0.05 ng/ml hCG values in two males aged 34 and 55 years were 0.058 and 0.078 ng/ml, respectively. A 23 and a 45 year old female had hCG levels of 0.230 and 0.117 ng/ml, respectively whereas hCG values in females aged between 51 and 60 were 0.185, 0.160, 0.078, 0.060, 0.068 and 0.057 ng/ml.

Detection of hCG immunoreactivity in normal subjects: We measured hCG binding activity in sera derived from 229 apparently healthy blood donors. Ten individuals were positive (>0.05 ng/ml). Calculated hCG values varied between 0.057 and 0.230 ng/ml as shown in table II.

Serial studies in patients with hCG producing tumors: We measured hCG levels in patients with hCG producing tumors and focused our studies on periods when hCG became undetectable (0.5 ng/ml) by a commercial assay. In this regard, we studied serial serum samples collected from twelve patients over a three to nine month period. hCG determinations were performed by both CM-IRMA and the assay based on anti-CTP antibodies. Results obtained by CM-IRMA are shown on FIG. 4 (top). In one patient treated for a testicular tumor, hCG values fell below the lower limit of sensitivity of the method (0.5 ng/ml) after 5 months of follow-up and remained around this limit for 10 weeks. Subsequently increasing hCG values signaled a recurrence of the tumor. In another patient treated for hydatidiform mole hCG levels rapidly decreased following chemotherapy and remained undetectable by the CM-IRMA assay for 7 months. This patient has had no recurrence of tumor for more than one year. Results of the anti-CTP antibody based assay performed on the same samples are shown on FIG. 4 (bottom). In a patient with a recurence of testicular tumor, hCG values were found to be consistantly above the lower limit of sensitivity of the assay and presumably signified the continued presence of tumor. The second patient had no recurrence of her trophoblastic disease and hCG values fell from 0.5 ng/ml to 0.05 ng/ml within 5 months and then remained undetectable thereafter. These results suggest the absence of tumor.

We then measured hCG by the anti-peptide based M-IRMA in sera of ten patients which had undetectable levels by the CM-IRMA. Results are shown in FIG. 5. It is important to emphasize that, except in two instances (patient A, hCG >50 ng/ml; patient B,m hCG =2.5 ng/ml), all hCG values presented in this figure were found to be below the lower limit of sensitivity of the CM-IRMA. Two patients treated by chemotherapy for hydatidiform mole (patients A and B) had hCG levels constantly above 0.05 nb/ml before a subsequent rise of hCG values. In one of these two patients the rise was due to pregnancy following a course of chemotherapy (patient A). In the other increasing levels of hCG preceded clinical evidence of tumor recurrence. hCG was detectable by anti-peptide based M-IRMA for periods of two to eight weeks in patients with gestational choriocarcinoma (patients F and H), hydatidiform mole (patients C, D, G, I, J) or ovarian tumor (patient E; dysembryoma). All these patients have been treated by chemotherapy; subsequently hCG levels became undetectable (<0.05 ng/ml). Furthermore none of these eight patients developed recurrent disease during follow-up periods of four to six months (patients D, E, G, I) or six to twelve months (patients C, F, H, J).

What is claimed as new and intended to be protected by Letters Patent of the United States is:

1. A method for the determination of human chorionic gonadotropin in a sample, which comprises:
   (a) contacting said sample with a first capture monoclonal antibody and a second capture monoclonal antibody which are bound on a carrier, wherein said first and second capture monoclonal antibodies are epitopically specific and non cross-reactive for distinct epitopes of the carboxy terminus region of the beta-subunit of human chorionic gonadotropin;
   (b) incubating the components of step (a) for a period of time and under conditions sufficient to form an immune complex between said human chorionic gonadotropin, said first capture monoclonal antibody, said second capture monoclonal antibody and said carrier,
   (c) adding to said complex of step (b) a detectably labeled indicator monoclonal antibody, wherein said indicator monoclonal antibody is epitopically specific for the alpha-subunit of human chorionic gonadotropin; and
   (d) determining the detectably labeled indicator monoclonal antibody in said carrier or in liquid phase, which is indicative of the amount of human chorionic gonadotropin in said sample.

2. The method of claim 1 wherein at least one of said first and second capture antibodies has a Kasn for hCG which is equal to or greater than about $10^8$/M but less than about $10^9$/M.

3. The method of claim 1 wherein at least one of said first and second capture antibodies has a Kasn for hCG which is equal to or greater than about $10^9$/M.

4. The method of claim 1 wherein said first capture monoclonal antibody is secreted by cell line FB12 and said second capture monoclonal antibody is secreted by a cell line selected from the group consisting of FB08 and FB09.

5. The method of claim 1 wherein said first capture monoclonal antibody is secreted by cell line FB12 and said second capture monoclonal antibody is derived from cell line FB09.

6. The method of claim 1 wherein said indicator monoclonal antibody is secreted by cell line HT 13.

7. The method of any of claims 2, 3 or 4 wherein said indicator monoclonal antibody is secreted by cell line HT 13.

8. The method of claim 5 wherein said indicator monoclonal antibody is secreted by cell line HT 13.

9. A kit useful for the detection of human chorionic gonadotropin comprising carrier means being compartmentalized to receive in close confinement therein one or more containers wherein:
   (a) a first container contains a first capture monoclonal antibody and a second capture monoclonal antibody which are bound on a carrier, wherein said first and second capture monoclonal antibodies are epitopically specific and noncross reactive for distinct epitopes of the carboxy terminus region of the beta-subunit of human chorionic gonadotropin; and
   (b) a second container contains a detectably labeled indicator monoclonal antibody, wherein said indicator monoclonal antibody is epitopically specific for the alpha-subunit of human chorionic gonadotropin.

10. The kit of claim 9 wherein at least one of said first and second capture antibodies has a Kasn for hCG which is equal to or greater than about $10^8$/M but less than about $10^9$/M.

11. The kit of claim 9 wherein at least one of said first and second capture antibodies has a Kasn for hCG which is equal to or greater than about $10^9$/M.

12. The kit of claim 9 wherein said first capture monoclonal antibody is secreted by cell line FB12 and said second capture monoclonal antibody is secreted by a cell line selected from the group consisting of FB08 and FB09.

13. The kit of claim 9 wherein said first capture monoclonal antibody is secreted by cell line FB12 and said second capture monoclonal antibody is secreted by cell line FB09.

14. The kit of claim 9 wherein said indicator monoclonal antibody is secreted by cell line HT 13.

15. The kit of any of claims 10, 11 or 12 wherein said indicator monoclonal antibody is secreted by cell line HT 13.

16. The kit of claim 13 wherein said indicator monoclonal antibody is secreted by cell line HT 13.

17. An insoluble immunological reagent support useful in the determination of human chorionic gonadotropin in a sample, which comprises an insoluble support comprising two immobilized capture monoclonal antibodies epitopically specific and non cross-reactive for distinct epitopes of the carboxy terminal region of the beta-subunit of human chorionic gonadotropin.

18. The reagent of claim 17 wherein at least one of said immobilized capture monoclonal antibodies has a Kasn for hCG which is equal to or greater than about $10^8$/M but less than about $10^9$/M.

19. The reagent of claim 17 wherein at least one of said immobilized capture monoclonal antibodies has a Kasn for hCG which is equal to or greater than about $10^9$/M.

20. The reagent of claim 17 wherein the first of said immobilized capture monoclonal antibodies is secreted by cell line FB12, and the second of said immobilized capture monoclonal antibodies is secreted by a cell line selected from the group consisting of FB08 and FB09.

21. The reagent of claim 17 wherein the first of said immobilized capture monoclonal antibodies is secreted by cell line FB12 and the second of said immobilized capture monoclonal antibodies is secreted by cell line FB09.

22. The cell line FB08.
23. The cell line FB09.
24. The cell line FB12.
25. The cell line HT 13.
26. The monoclonal antibody secreted by cell line FB08.
27. The monoclonal antibody secreted by cell line FB09.
28. The monoclonal antibody secreted by cell line FB12.
29. The monoclonal antibody secreted by cell line HT 13.

* * * * *